United States Patent [19]

Zaiger

[11] Plant 4,237

[45] Apr. 11, 1978

[54] APRICOT TREE

[76] Inventor: Chris Floyd Zaiger, 537 Rosemore Ave., Modesto, Calif. 95351

[21] Appl. No.: 709,612

[22] Filed: Jul. 28, 1976

[51] Int. Cl.[2] ..... A01H 5/03
[52] U.S. Cl. ..... Plt./39
[58] Field of Search ..... Plt./39

*Primary Examiner*—Robert E. Bagwill

[57] ABSTRACT

A variety of apricot tree which has dwarf characteristics, close leaf nodes, short heavy branches, stocky trunk, and bears yellow flesh, freestone fruit. The tree height being approximately 30% of a normal apricot tree.

3 Drawing Figures

ORIGIN OF THE VARIETY

The present variety of dwarf apricot tree is a bud sport from an open pollenated seedling of Flaming Gold Apricot (U.S. Plant Pat. No. 2,822) grown by me in my experimental orchard located near Modesto, Calif. Subsequent to recognition by me of the novel characteristics which will hereinafter appear of said bud sport, I selected and propagated the variety to meet the existing demand for a dwarf apricot tree bearing medium size fruit of good eating quality.

ASEXUAL REPRODUCTION OF THE VARIETY

Asexual reproduction of the new variety by budding, as performed at Modesto, Calif., shows that said characteristics come true to form as are established and transmitted through succeeding propagations.

SUMMARY OF THE VARIETY

The present variety of apricot tree bears medium size fruit of good eating quality. The tree being of dwarf characteristics, pruning, thinning and harvesting operations could be conducted without the use of ladders and by a person standing on the ground adjacent the tree.

BRIEF DESCRIPTION OF THE PHOTOGRAPHS

The accompanying photographs show a typical specimen of the foliage and fruit of my new variety, with upper and lower surfaces of the foliage being illustrated and exterior and sectional view of the fruit being shown. These illustrations were taken shortly after being picked at maturity. The colors are as nearly true as is reasonably possible in a color representation of this type. The second sheet of drawings shows the dwarf habit of my variety in comparison with Tilton, both plants being of the same age and grown under the same conditions.

DESCRIPTION OF THE VARIETY

The following is a detailed description of the foliage and fruit of my new variety, as based upon observation of specimens grown in Modesto, Calif., with color terminology in accordance with Reinhold Color Atlas by A. Kornerup and J. H. Wanscher.

Tree:
- *Size.*—Dwarf. Average height — 6–8 feet.
- *Vigor.*—Non-vigorous.
- *Form.*—Spreading.
- *Production.*—Productive.

Branches:
- *Size.*—Stocky. Upright.
- *Lenticels.*—Present.
- *Color.*—Light brown (6-D-4).

Leaves:
- *Size.*—Medium to large. Average Length $2\frac{3}{4}''$ to $3\frac{3}{4}''$. Average width — $1\frac{7}{8}''$ to $2\frac{3}{8}''$.
- *Form.*—Ovate to orbicular. Abruptly pointed.
- *Internodes.*—Short — approximately $\frac{1}{2}$ inch between nodes.
- *Margin.*—Serrate.
- *Petiole.*—Average length — $\frac{3}{4}''$.
- *Glands.*—Number 2 to 6. Primarily located on petiole.
- *Color.*—Under surface (28-D-5). Upper surface (28-E-8).

Flower buds:
- *Size.*—Medium to small.
- *Shape.*—Short, plump.

Flowers:
- *Date of First Bloom.*—Feb. 18, 1976 to Feb. 28, 1976. Varies from year to year due to weather variations.
- *Size.*—Medium.
- *Color.*—Light pink, fades to nearly white at petal fall.

Fruit.
- *Maturity.*—Eating ripe. The second week of June.
- *Size.*—Only slightly variable. Average axially diameter $1\frac{3}{4}''$. Average transverse diameter in suture plane — $2\frac{1}{4}''$. Average diameter measured at right angles to the suture plane $1\frac{1}{2}''$.
- *Form.*—Slightly variable. Symmetrical. Globose. Somewhat compressed laterally toward suture.
- *Suture.*—Shallow; extends from stem to blossom end. Terminating at blossom end.
- *Cavity.*—From rounded to somewhat elongated in suture plane. Average depth $\frac{1}{8}''$. Average breadth 3/16".
- *Apex.*—Rounded to slightly depressed.
- *Base.*—Rounded.

Skin:
- *Thickness.*—Thin.
- *Texture.*—Tender, moderately smooth. Tenacious to flesh.
- *Down.*—Scant. Very short.
- *Color.*—Is from deep orange (6-A-8) to mandarin orange (6-B-8).
- *Tendency to Crack.*—None.

Flesh:

*Color.*—Is from persian orange (6-A-7) to deep orange (6-A-8).

*Flavor.*—Predominantly apricot.

*Texture.*—Firm, meaty.

*Ripens.*—Generally even.

*Eating quality.*—Good.

*Aroma.*—Not pronounced.

Stone:

*Type.*—Free.

*Size.*—Medium. Average length — $1\frac{1}{8}''$. Average breadth — $\frac{3}{4}''$. Average thickness — $\frac{1}{2}''$.

*Form.*—Ovoid. Very slightly cuneate toward apex.

*Surfaces.*—Regularly pitted, only slightly throughout.

*Ridges.*—Two ridges extending approximately 180° across surface of stone on both sides of suture plane and approximately 28° displaced from each other.

*Color.*—Varies slightly light brown (7-D-5) to brown (7-E-6).

*Splitting tendency.*—None.

Use: Home canning. Market. Drying.

Keeping quality. Very good.

Shipping quality: Good.

The tree and its fruit herein described may vary in slight detail due to climate, cultural practices, and soil conditions under which this variety may be grown; the present description being of the variety as grown in the Central Valley of California.

I claim:

1. A new and distinct variety of apricot tree, as illustrated and described, characterized by its dwarf size, averaging approximately four feet in height in four years and reaching a mature height of 6 to 8 feet, its leaf nodes being approximately $\frac{1}{2}$ inch apart on the new variety as compared to $\frac{7}{8}$ of an inch on the standard apricot variety Tilton, and the new apricot variety is further characterized by the productive bearing of medium size fruit of good quality and firmness.

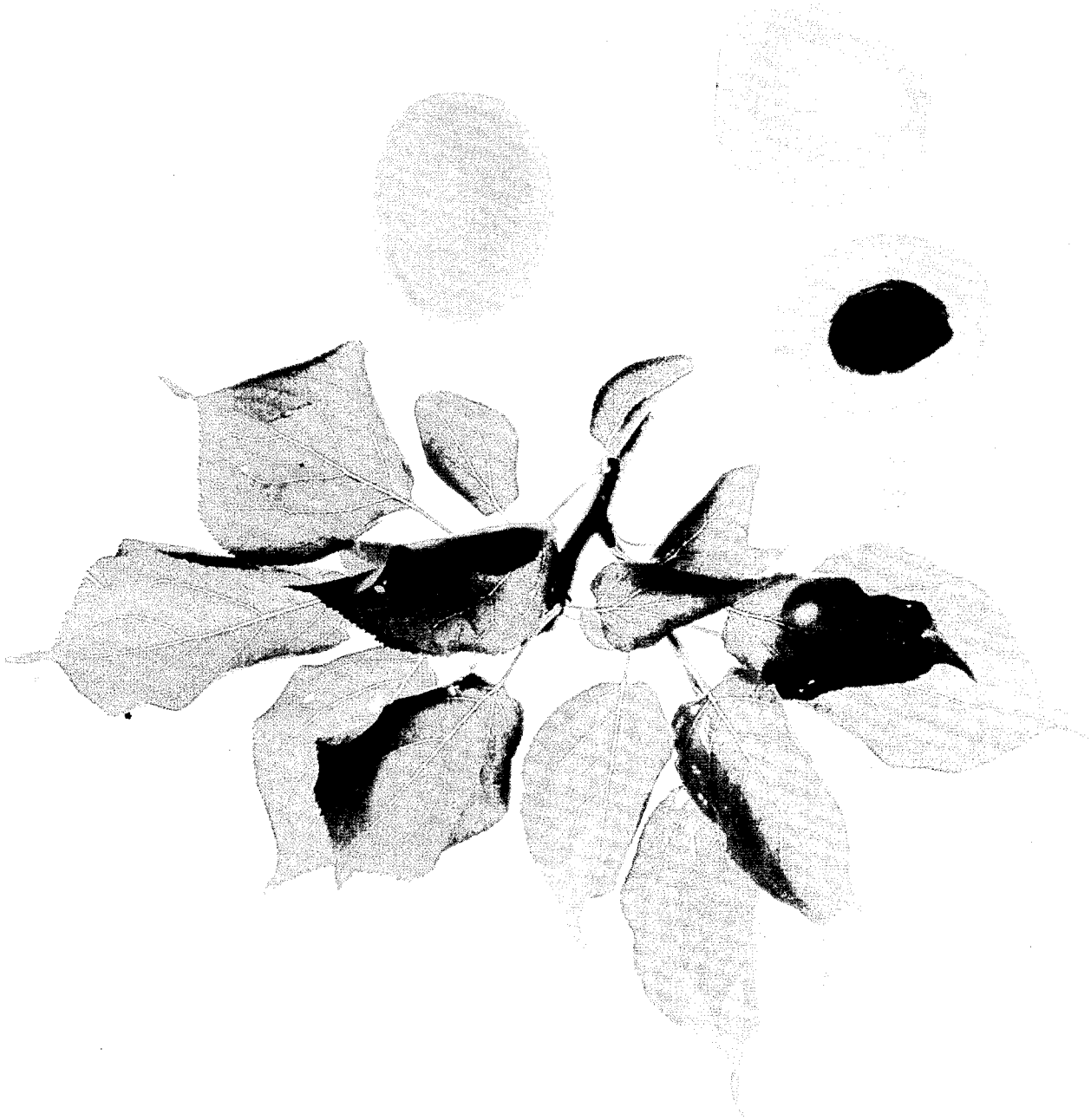

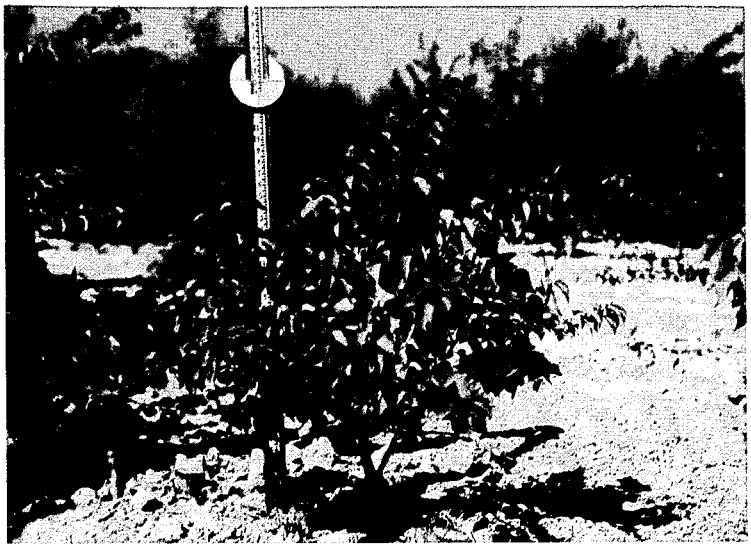
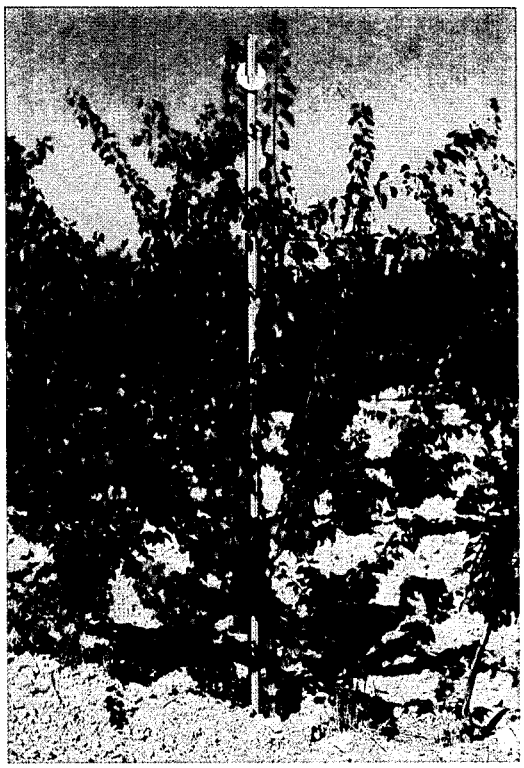

* * * * *